United States Patent
Warner et al.

(10) Patent No.: US 6,281,407 B1
(45) Date of Patent: Aug. 28, 2001

(54) PERSONAL CARE PRODUCT CONTAINING A PRODUCT AGENT

(75) Inventors: Steven Bruce Warner, South Dartmouth, MA (US); James Arthur Davis, Roswell, GA (US); Sharon Linda Greene, Canton, GA (US); Rosann Marie Kaylor, Cumming, GA (US); Pamela Jean Mayberry, Roswell, GA (US); Michael Tod Morman, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/322,420

(22) Filed: May 28, 1999

(51) Int. Cl.$^7$ ........................................... A61F 13/15
(52) U.S. Cl. ................................... 604/367; 604/385.01
(58) Field of Search ............................ 604/364, 367, 604/375, 358, 385.01

(56) References Cited

U.S. PATENT DOCUMENTS

| | | | |
|---|---|---|---|
| 2,230,903 | 2/1941 | Ostenberg | 128/156 |
| 2,242,937 | 5/1941 | Biederman | 128/285 |
| 3,093,546 | 6/1963 | Atkinson | 167/84 |
| 3,338,992 | 8/1967 | Kinney | 264/24 |
| 3,341,394 | 9/1967 | Kinney | 161/72 |
| 3,381,688 | 5/1968 | Satas | 128/296 |
| 3,502,763 | 3/1970 | Hartmann | 264/210 |
| 3,542,615 | 11/1970 | Dobo et al. | 156/181 |
| 3,692,618 | 9/1972 | Dorschner et al. | 161/72 |
| 3,802,817 | 4/1974 | Matsuki et al. | 425/66 |
| 3,802,909 * | 4/1974 | Rockett et al. | 117/100 |
| 3,849,241 | 11/1974 | Butin et al. | 161/169 |
| 3,957,971 | 5/1976 | Oleniacz | 424/70 |
| 3,994,298 | 11/1976 | Des Marais | 128/285 |
| 4,035,540 | 7/1977 | Gander | 428/198 |
| 4,061,145 | 12/1977 | Des Marais | 128/275 |
| 4,061,846 * | 12/1977 | Gross et al. | 526/16 |
| 4,062,451 | 12/1977 | Gander | 206/524.2 |
| 4,199,068 * | 4/1980 | Weitzner | 211/49 |
| 4,272,422 * | 6/1981 | Tanaka | 260/29.6 |
| 4,335,722 * | 6/1982 | Jackson | 128/285 |
| 4,340,563 | 7/1982 | Appel et al. | 264/518 |
| 4,485,133 * | 11/1984 | Ohtsuka et al. | 428/38 |
| 4,643,179 | 2/1987 | Wang | 128/156 |
| 4,793,336 | 12/1988 | Wang | 128/156 |
| 4,826,497 | 5/1989 | Marcus et al. | 604/359 |
| 4,853,086 | 8/1989 | Graef | 162/157.6 |
| 4,880,417 | 11/1989 | Yabrov et al. | 604/355 |
| 4,880,886 * | 11/1989 | Kondo et al. | 526/80 |
| 5,035,731 | 7/1991 | Spruill et al. | 55/387 |
| 5,037,459 | 8/1991 | Spruill et al. | 55/387 |
| 5,057,368 | 10/1991 | Largman et al. | 428/397 |
| 5,069,970 | 12/1991 | Largman et al. | 428/373 |
| 5,108,820 | 4/1992 | Kaneko et al. | 428/198 |
| 5,108,827 | 4/1992 | Gessner | 428/219 |
| 5,137,525 | 8/1992 | Glassman | 604/385.1 |
| 5,143,773 | 9/1992 | Takuno | 428/137 |
| 5,165,947 * | 11/1992 | Colucci et al. | 426/124 |
| 5,183,872 * | 2/1993 | Heidel et al. | 527/300 |
| 5,190,533 | 3/1993 | Blackburn | 604/367 |
| 5,277,976 | 1/1994 | Hogle et al. | 428/397 |
| 5,336,552 | 8/1994 | Strack et al. | 428/224 |
| 5,364,382 | 11/1994 | Latimer et al. | 604/378 |
| 5,378,832 * | 1/1995 | Kurane et al. | 536/123.1 |
| 5,382,400 | 1/1995 | Pike et al. | 264/168 |
| 5,449,551 | 9/1995 | Taniguchi | 428/288 |
| 5,466,410 | 11/1995 | Hills | 264/172.11 |
| 5,490,846 | 2/1996 | Ellis et al. | 604/366 |
| 5,575,785 | 11/1996 | Gryskiewicz et al. | 604/385.2 |
| 5,637,105 | 6/1997 | Tanaka et al. | 604/368 |
| 5,693,411 * | 12/1997 | Hansen et al. | 428/283 |
| 5,695,376 * | 12/1997 | Datta et al. | 442/334 |
| 5,700,254 * | 12/1997 | McDowall et al. | 604/378 |
| 5,700,553 * | 12/1997 | Cohen et al. | 428/220 |
| 5,713,881 * | 2/1998 | Rezai et al. | 604/368 |
| 5,718,697 | 2/1998 | Chauvette et al. | 604/367 |
| 5,860,428 | 1/1999 | Lesser et al. | 131/331 |
| 5,876,388 * | 3/1999 | McDowall et al. | 604/384 |
| 5,925,439 * | 7/1999 | Haubach | 428/178 |
| 5,928,665 * | 7/1999 | Cercone | 424/445 |
| 5,976,995 * | 11/1999 | Palmer, Jr. | 442/118 |
| 6,004,307 * | 12/1999 | Colon et al. | 604/385.1 |
| 6,018,093 * | 1/2000 | Roe et al. | 604/367 |

FOREIGN PATENT DOCUMENTS

| | | | |
|---|---|---|---|
| 0 449 267 | 10/1991 | (EP) | B32B/33/00 |
| 0 531 096 | 10/1997 | (EP) | A61F/13/00 |
| 0 802 238 | 10/1997 | (EP) | C08L/101/14 |
| 0 806 195 | 11/1997 | (EP) | A61F/13/15 |
| 87165 | 9/1991 | (IL) . | |
| 92/10923 | 12/1992 | (KR) . | |
| 92/10924 | 12/1992 | (KR) . | |
| 99/12530 | 3/1999 | (WO) | A61K/9/70 |

OTHER PUBLICATIONS

Van Nostrand's Scientific Encyclopedia, 6$^{th}$ ed., p. 870.
Polymer Blends and Composites by John A. Manson and Leslie H. Sperling, copyright 1976 by Plenum Press, a division of Plenum Publishing Corporation of New York, IBSN 0–306–30831–2, at pp. 273 through 277.

* cited by examiner

Primary Examiner—Dennis Ruhl
Assistant Examiner—Jamisue Webb
(74) Attorney, Agent, or Firm—James B. Robinson

(57) ABSTRACT

There is provided a personal care product having a drying agent incorporated into it. The drying agent can reduce or control the relative humidity in the air enclosed by a personal care product significantly. Such a drying agent may be a desiccant or humectant or a combination of both. The drying agent may function using chemical or physical means and may be in fibrous, particulate or other form. The reduction of the relative humidity within a personal care product will reduce skin hydration which is believed to reduce redness and irritation due to contact with fluids.

7 Claims, No Drawings

PERSONAL CARE PRODUCT CONTAINING A PRODUCT AGENT

FIELD OF THE INVENTION

This invention relates to absorbent articles, particularly absorbent structures that are useful in personal care products such as disposable diapers, incontinence guards, childcare training pants and the like. (The reference to "diapers" in the title is merely illustrative). More particularly, the invention relates to absorbent articles that reduce the hydration of the skin by reducing and/or controlling the relative humidity (RH) in the air within the article's enclosure through the use of drying agents. This removes water vapor from the area between the article and the skin and, as a result, aids the skin in its fight against the detrimental effect of bodily exudates and mechanical abrasion.

BACKGROUND OF THE INVENTION

Personal care products are absorbent articles including diapers, training pants, incontinence devices and the like. These products are designed to absorb and contain body exudates and are generally single-use or disposable items which are discarded after a relatively short period of use—usually a period of hours—and are not intended to be washed and reused. Such products are placed against or in proximity to the wearer's body to absorb and contain various exudates discharged from the body. All of these products typically include a liquid permeable bodyside liner or cover, a liquid impermeable outer cover or backsheet, and an absorbent structure disposed between the bodyside liner and outer cover. The liquid impermeable outer cover may be breathable, i.e., permeable to water vapor, but typically is not.

It has been found that urination can occur at rates as high as 15 to 20 milliliters per second and at velocities as high as 280 centimeters per second. The volume of urine released per occurrence can vary from about a nominal amount to about 100 ml. It's important for the absorbent article to rapidly uptake liquid to avoid excessive pooling of liquid on the body-facing surface of the bodyside liner in order to avoid leakage. Even if absorbed, however, any liquid in the article contributes to the overall relative humidity near the wearer' skin, causing discomfort and potential skin health problems due to excessive skin hydration.

The problem of high relative humidity near the skin in an absorbent article has been addressed in the art through a number of means. U.S. Pat. No. 5,137,525 for example, uses mechanical means to increase airflow in the article. Breathable outer covers allow air and water vapor diffusion into and out of the absorbent article's enclosure and have been mentioned previously.

Despite these attempts, the need exists for further improvement in the reduction of skin hydration within absorbent articles. In particular, there is a need for drying agents that can remove water vapor from the air within an article near the skin. The present invention provides for such reduced relative humidity and skin hydration within an absorbent article's enclosure.

SUMMARY OF THE INVENTION

A personal care product having a drying agent incorporated into it achieves the objects of this invention. The drying agent can reduce or control the relative humidity in the air within a personal care product significantly. Such a drying agent is a desiccant or a humectant or a combination of both, and might be melt processable so that it may be used in modern fiber forming processes like spunbonding and meltblowing. The drying agent may alternatively be placed in a bag and inserted below the liner in a personal care product. If in particulate form, a drying agent could be attached to the fibers of a web like the liner or to a superabsorbent/pulp layer through the use of an adhesive or binder.

The reduction or control of the relative humidity within a personal care product presumably reduces skin hydration which is believed to reduce redness and irritation due to contact with fluids.

DEFINITIONS

"Disposable" includes being disposed of after usually a single use and not intended to be washed and reused.

"Hydrophilic" describes fibers or the surfaces of fibers, which are wetted by the aqueous liquids in contact with the fibers. The degree of wetting of the materials can, in turn, be described in terms of the contact angles and the surface tensions of the liquids and materials involved. A Cahn SFA-222 Surface Force Analyzer System or a substantially equivalent system can provide equipment and techniques suitable for measuring the wettability of particular fiber materials. When measured with this system, fibers having contact angles less than 90° are designated "wettable" or hydrophilic, while fibers having contact angles equal to or greater than 90° are designated "nonwettable" or hydrophobic.

"Layer" when used in the singular can have the dual meaning of a single element or a plurality of elements.

"Liquid" means a nongaseous substance and/or material that flows and can assume the interior shape of a container into which it is poured or placed.

"Liquid communication" means that liquid such as urine is able to travel from one location to another location.

"Particles" refers to any geometric form such as, but not limited to, spherical grains, cylindrical fibers or strands, or the like.

"Spray" and variations thereof include forcefully ejecting liquid, either as a stream such as swirl filaments, or atomized particles through an orifice, nozzle, or the like, by means of an applied pressure using air or other gas, by force of gravity, or by centrifugal force. The spray can be continuous or non-continuous.

"Relative humidity" refers to the ratio of the quantity of water vapor present in the atmosphere to the quantity that would saturate at the existing temperature. It is also the ratio of the pressure of water vapor present to the pressure of saturated water vapor at the same temperature.

"Spunbonded fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 30 microns. The fibers may also have shapes such as those described in U.S. Pat.

No. 5,277,976 to Hogle et al., U.S. Pat. No. 5,466,410 to Hills and U.S. Pat. Nos. 5,069,970 and 5,057,368 to Largman et al., which describe fibers with unconventional shapes.

"Meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241. Meltblown fibers are microfibers which may be continuous or discontinuous, and are generally smaller than 10 microns in average diameter.

"Conjugate fibers" refers to fibers which have been formed from at least two polymer sources extruded from separate extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such a conjugate fiber may be, for example, a sheath/core arrangement wherein one polymer is surrounded by another or may be a side by side arrangement, a pie arrangement or an "islands-in-the-sea" arrangement. Conjugate fibers are taught in U.S. Pat. No. 5,108,820 to Kaneko et al., U.S. Pat. No. 5,336,552 to Strack et al., and U.S. Pat. No. 5,382,400 to Pike et al. For two component fibers, the polymers may be present in ratios of 75/25, 50/50, 25/75 or any other desired ratios.

"Biconstituent fibers" refers to fibers, which have been formed from at least two polymers extruded from the same extruder as a blend. The term "blend" is defined below. Biconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Biconstituent fibers are sometimes also referred to as multiconstituent fibers. Fibers of this general type are discussed in, for example, U.S. Pat. No. 5,108,827 to Gessner. Bicomponent and biconstituent fibers are also discussed in the textbook *Polymer Blends and Composites* by John A. Manson and Leslie H. Sperling, copyright 1976 by Plenum Press, a division of Plenum Publishing Corporation of New York, IBSN 0-306-30831-2, at pages 273 through 277.

"Bonded carded web" refers to webs that are made from staple fibers which are sent through a combing or carding unit, which separates or breaks apart and aligns the staple fibers in the machine direction to form a generally machine direction-oriented fibrous nonwoven web. Such fibers are usually purchased in bales, which are placed in an opener/ blender, or picker, which separates the fibers prior to the carding unit. Once the web is formed, it then is bonded by one or more of several known bonding methods. One such bonding method is powder bonding, wherein a powdered adhesive is distributed through the web and then activated, usually by heating the web and adhesive with hot air. Another suitable bonding method is pattern bonding, wherein heated calender rolls or ultrasonic bonding equipment are used to bond the fibers together, usually in a localized bond pattern, though the web can be bonded across its entire surface if so desired. Another suitable and well-known bonding method, particularly when using conjugate staple fibers, is through-air bonding.

"Airlaying" is a well-known process by which a fibrous nonwoven layer can be formed. In the airlaying process, bundles of small fibers having typical lengths ranging from about 3 to about 19 millimeters (mm) are separated and entrained in an air supply and then deposited onto a forming screen, usually with the assistance of a vacuum supply. The randomly deposited fibers then are bonded to one another using, for example, hot air or a spray adhesive.

"Drying Agent" means a material that will reduce the relative humidity in air or maintain the relative humidity at a value lower than it would be without the presence of the drying agent.

"Desiccant" means a material that will reduce the relative humidity in air to a value lower than it would be without the presence of the desiccant, preferably to a very low level, e.g. less than 25 percent.

"Humectant" means a material that will maintain the relative humidity at a value lower than it would be without the presence of the humectant. This level is preferably at about 85 percent in order to promote skin health.

"Personal care product" means diapers, training pants, absorbent underpants, adult incontinence products and other such articles.

DETAILED DESCRIPTION

Traditional absorbent systems for personal care products may be generalized as having the functions of surge control and containment (retention) or SC.

Surge control materials, the "S" in SC, are provided to quickly accept the incoming insult and either absorb, hold, channel or otherwise manage the liquid so that it does not leak outside the article. The surge layer may also be referred to as an intake layer, transfer layer, transport layer and the like. A surge material must typically be capable of handling an incoming insult of between about 60 and 100 cc at an insult volumetric flow rate of from about 5 to 20 cc/sec, for infants, for example.

Containment or retention materials, the "C" in SC, must absorb the insult quickly and efficiently. They are in liquid communication with the surge layer and should be capable of pulling the liquid from the surge layer and absorbing the liquid without significant blocking of penetration of liquid further into the absorbent. Retention materials are often high rate superabsorbent materials such as blends of polyacrylate superabsorbent and fluff. These materials rapidly absorb and hold liquid.

In addition to the surge control and containment materials in traditional absorbent systems, recent work has introduced another layer interposed between the S and C layers and in liquid communication with them. This new layer is a distribution layer, producing a system with surge control, distribution and containment or "SDC".

Distribution materials, the "D" in SDC, must be capable of moving fluid from the point of initial deposition to where storage is desired. Distribution must take place at an acceptable rate such that the target insult area, generally the crotch area, is ready for the next insult. By "ready for the next insult" it is meant that sufficient liquid has been moved out of the target zone so that the next insult results in liquid absorption and runoff within acceptable volumes. The time between insults can range from just a few minutes to hours, generally depending on the age of the wearer.

Absorbent products such as, for example, diapers, generally also have a liner which goes against the wearer and a backsheet which is the most exterior layer. An absorbent product may also contain other layers as well.

The liner is sometimes referred to as a bodyside liner or topsheet and is adjacent the surge material. In the thickness direction of the article, the liner material is the layer against the wearer's skin and so the first layer in contact with liquid or other exudate from the wearer. The liner further serves to isolate the wearer's skin from the liquids held in an absorbent structure and should be compliant, soft feeling and non-irritating.

Various materials can be used in forming the bodyside liner of the present invention, including apertured plastic films, woven fabrics, nonwoven webs, porous foams, reticulated foams and the like. Nonwoven materials have been found particularly suitable for use in forming the bodyside liner. These include spunbond or meltblown webs of polyolefin, polyester, polyamide (or other like fiber forming polymer) filaments, or bonded carded webs of natural polymers (for example, rayon or cotton fibers) and/or synthetic polymers (for example, polypropylene or polyester) fibers. The nonwoven web can be surface treated with a selected amount of surfactant, such as TRITON® X-102 or ACHOVEL® surfactant in an amount between about 0.05 and 0.5 weight percent, or otherwise processed to impart the desired level of wettability and hydrophilicity. If a surfactant is used, it can be an is internal additive that migrates to the surface or applied to the web by any conventional means, such as spraying, printing, dipping, brush coating and the like.

The surge layer is most typically interposed between and in intimate, liquid communicating contact with the bodyside liner and another layer such as a distribution or retention layer. The surge layer is generally subjacent the inner (unexposed) surface of bodyside liner. To further enhance liquid transfer, it can be desirable to attach the upper and/or lower surfaces of the surge layer to the liner and the distribution layer, respectively. Suitable conventional attachment techniques may be utilized, including without limitation, adhesive bonding (using water-based, solvent-based and thermally activated adhesives), thermal bonding, ultrasonic bonding, needling and pin aperturing, as well as combinations of the foregoing or other appropriate attachment methods. If, for example, the surge layer is adhesively bonded to the bodyside liner, the amount of adhesive add-on should be sufficient to provide the desired level(s) of bonding, without excessively restricting the flow of liquid from the liner into the surge layer. Various woven and nonwoven webs and foams can be used to construct a surge layer. For example, the surge layer may be a nonwoven fabric layer composed of a meltblown or spunbond web of polyolefin filaments. Such nonwoven fabric layers may include conjugate, biconstituent and homopolymer fibers of staple or other lengths and mixtures of such fibers with other types of fibers. The surge layer also can be a bonded-carded web or an airlaid web composed of natural and/or synthetic fibers. The bonded-carded web may, for example, be a powder bonded carded web, an infrared bonded carded web, or a through-air bonded carded web. Further examples of surge materials may be found in U.S. Pat. No. 5,490,846 to Ellis et al. and in U.S. Pat. No. 5,364,382 to Latimer. Surge layers may be composed of a substantially hydrophobic material, and the hydrophobic material may optionally be treated with a surfactant or otherwise processed to impart a desired level of wettability and hydrophilicity. Surge layers can have a generally uniform thickness and cross-sectional area.

A distribution layer, if present, must be capable of moving fluid from the point of initial deposition to where storage is desired. Distribution must take place at an acceptable rate such that the target insult area, generally the crotch area, is ready for the next insult. The time between insults can range from just a few minutes to hours, generally depending on the age of the wearer. Materials from which the distribution layer may be made include woven fabrics and nonwoven webs. For example, the distribution layer may be a non-woven fabric layer composed of a meltblown or spunbond web of polyolefin, polyester, polyamide (or other web-forming polymer) filaments. Such nonwoven fabric layers may include conjugate, biconstituent and homopolymer fibers of staple or other lengths and mixtures of such fibers with other types of fibers. The distribution layer also can be a bonded-carded web, an airlaid web or a wetlaid pulp structure composed of natural and/or synthetic fibers or a combination thereof.

Retention materials are typically cellulosic materials or superabsorbents or mixtures thereof. Such materials are usually designed to quickly absorb liquids and hold them, usually without release. Superabsorbents are commercially available from a number of manufactures including Dow Chemical Company of Midland, Mich. and Stockhausen Corporation of Greensboro, N.C. Retention materials may be zoned and their compositions chosen to move liquids away from the target zone to more remote storage locations. Such a design more efficiently uses the entire absorbent article.

The backsheet is sometimes referred to as the outer cover and is the farthest layer from the wearer. The outer cover is typically formed of a thin thermoplastic film, such as polyethylene film, which is substantially impermeable to liquid. The outer cover functions to prevent body exudates contained in an absorbent structure from wetting or soiling the wearer's clothing, bedding, or other materials contacting the diaper. The outer cover may be, for example, a polyethylene film having an initial thickness of from about 0.5 mil (0.012 millimeter) to about 5.0 mil (0.12 millimeter). The polymer film outer cover may be embossed and/or matte finished to provide a more aesthetically pleasing appearance. Other alternative constructions for outer cover include woven or nonwoven fibrous webs that have been constructed or treated to impart the desired level of liquid impermeability, or laminates formed of a woven or nonwoven fabric and thermoplastic film. The outer cover may optionally be composed of a vapor or gas permeable microporous "breathable" material, that is permeable to vapors or gas yet substantially impermeable to liquid. Backings may also serve the function of a mating member for mechanical fasteners, in the case, for example, where a nonwoven fabric is the outer surface.

Despite the advantages of modem surge, distribution and retention materials, its been found that a small amount of liquid can still remain in contact with the skin for some time after urination into a personal care product. Even absent skin wetness, however, a higher relative humidity level persists in the product after urination. This exposure to liquid and/or high relative humidity levels in a personal care product is also believed to be detrimental to the skin. The inventors have found that the incorporation of a drying agent into a personal care article like a diaper can reduce skin hydration significantly by reducing the relative humidity in the air within a personal care product. It's believed this will have the effect of reducing redness and irritation of the skin. This is especially true when a new diaper is put on the wearer. If the skin were excessively hydrated when the new diaper was put on the wearer, the relative humidity in the diaper enclosure would rapidly increase in a conventional diaper, not allowing the skin to dry out and return to normal. The diaper of the present invention dries the skin to a more normal state of hydration.

There are two types or subclasses of drying agents suitable for the practice of this invention; desiccants and humectants.

Desiccants will remove water from the air until they are completely used whereas humectants function by trying to maintain a relative humidity at a pre-determined level.

In the case of desiccants, it is preferable that commercial personal care products like diapers be individually packaged so that they may be protected from environmental water vapor. Otherwise, the desiccant in the diaper may be completely used up by the time it is placed on a baby. The desiccant exposed to the environment may be used up during, for example, by storage in humid environments or by long storage periods even in relatively dry environments.

The reduction in skin hydration may occur after insult or may occur, for example, when a new diaper is placed on the wearer. After a new diaper is placed on the baby and before the first urination, a desiccant will remove water from the air within the product. After urination, the desiccant will continue to remove water vapor from within the product, however, two sources of water vapor, the skin and the diaper itself, will be present. In either case, water vapor removal and relative humidity reduction will continue until the desiccant is completely used. It may be desirable, in order to avoid contact between the liquid water or urine and the desiccant, to place the desiccant in a liquid impermeable but vapor permeable bag such as a bag made from meltblown fibers. In this way, the desiccant will remove only that moisture that is in vapor form and passes through the bag.

Desiccants using chemical absorption to function include $P_2O_5$, $Mg(ClO_4)_2$, $BaO$, $KOH$, $CaO$, $Al_2O_3$, $NaOH$, $CaBr_2$, $CaCl_2$, $Ba(ClO_4)_2$, $ZnCl_2$ and $ZnBr_2$, though because of safety concerns the most preferable desiccant is $Al_2O_3$. These chemicals may be placed within a personal care product such that they are exposed to the air within the product during use. Desiccants using physical adsorption, such as silica gel, may also be used. It would be preferable to use a material or component already present in a typical personal care product that could be made from or into a desiccant. The pulp and/or superabsorbent in the retention layer of a product, for example, may be super dried so that they are available to function as desiccants yet represent little change to current manufacturing methods and equipment. Super dried, in this context, means a material having a moisture content of 75 percent or less than it would have prior to being super dried. It's believed that the reduction in air humidity by a desiccant should be to less than 85 percent relative humidity.

In order to test the effectiveness of the invention a number of experiments were run and are discussed below:

EXPERIMENT 1

A standard diaper containing superabsorbent material was super dried in an environment of flowing, dry nitrogen at 92° C. for two days. The diaper was subsequently placed on a scale and weighed in an environment of about 20 percent relative humidity at room temperature and the weight gain data is given below.

| Time (min.) | Wt (gms) |
|---|---|
| 0 | 55.77 |
| 5 | 55.88 |
| 15 | 55.97 |
| 55 | 56.15 |
| 95 | 56.50 |
| 1200 | 57.22 |

EXPERIMENT 2

Armbands were placed on the arm of volunteers for 1 hour. These armbands had 3 grams of saline water per gram of fluff which hydrated the skin. After the hour, the wet armbands were replaced with a standard armband on one arm and a desiccated armband on another. The skin hydration was measured using the trans-epidermal water loss test, known to those skilled in the art and described in U.S. patent application Ser. No. 09/139,824, and showed the arm with the standard armband had a value of 0.27 $gms/m^2/hr$ after one hour and the arm with the desiccated armband had a value of 0.05 after one hour. The test was repeated using a different volunteer and the standard and desiccated armbands yielded results of 3.24 and 1.62 respectively. This shows that the desiccated armbands produced less hydrated skin than that of the standard armband.

EXPERIMENT 3

The arm was saturated in the same manner as in Experiment 2. After the hour, the wet armbands were replaced with a standard armband on one arm and a desiccated armband on another. The relative humidity was measured under the armband. The results are shown below with the first RH column representing the arm with the desiccated armband.

| Time (min.) | RH (%) | RH (%) |
|---|---|---|
| 0 | 92.9 | 96 |
| 1 | 8.4 | 93.2 |
| 2 | 4.5 | 93.1 |
| 3 | 3.3 | 93.1 |
| 5 | 3.1 | 92.3 |
| 60 | 9.1 | 90.7 |
| 40 | 7.7 | 92.5 |

These experiments show that desiccants can significantly reduce skin hydration and presumably improve skin health.

Humectants function by trying to maintain relative humidity at a pre-determined level as noted above. Once the pre-determined level has been reached the humectant will cease absorbing or desorbing water. If the level of humidity drops below the pre-determined level, the humectant will release water vapor in order to maintain the desired level of humidity, in contrast to the functioning of a desiccant, which will absorb water even at low relative humidity conditions. A humectant, therefore, can not only reduce the relative humidity level in a diaper; it can control or maintain the relative humidity at a desired value.

Typical humectants include glycerin, sorbitol, glycols, polyethylene glycol, propylene glycol, fructose, glucose, maltose, corn syrup, urea, and various chlorides.

If the humectant in a personal care product were chosen such that it maintained a relative humidity of less than about 85 percent, it would release moisture before use in the typical home since the humidity in a typical home is usually less than 85 percent. Once placed on a wearer, the humidity within the personal care product would most likely be over 85 percent, causing the dry humectant to absorb moisture to keep the humidity under control. Its believed by the inventors that a relative humidity of about 85 percent is quite beneficial to skin health so a personal care product with a humectant designed to maintain such a humidity would be a positive measure. Should future research reveal that a different relative humidity is ideal for skin health, the proper humectant could be chosen in order to deliver that humidity level.

It is also possible to combine the two types of drying agents, desiccants and humectants, in one personal care product. This would provide the advantages of both agents and result in a product, e.g. a diaper, that rapidly absorbed water vapor when initially placed on an infant through the action of a desiccant and thereafter maintained a certain relative humidity level through the action of a humectant.

The layer that the drying agent would be incorporated into is preferably the liner layer. This layer is closest to the skin of a wearer where regulation of relative humidity is most critical. An ideal candidate would also be elastic so that it could adjust to the movement of the wearer without bunching or binding. If the drying agent were melt processable, the liner could be spun from the agent and used directly against the skin. If not, a drying agent could be placed in a bag of, for example, meltblown fibers, and the bag placed below the liner. A meltblown bag would keep the drying agent from coming in contact with liquid water but would allow water vapor to enter and be absorbed by the drying agent.

Certain drying agents may be suitable for modern fiber forming processes so that they may be simply and directly incorporated into a product, as many of the individual pieces of many personal care products are produced by various fiber forming techniques like meltblowing and spunbonding. The drying agents may also be added as particles to polymers for fiber forming using a polymer that is permeably to water vapor so that it may pass through the polymer and reach the particle. They may alternatively be added to a fibrous web using the bonding and carding and airlaying methods, for example. It may also be possible to incorporate a drying agent into the containment component present in most personal care products, as part of the superabsorbent and/or pulp or mixed with them as another material. If in particulate form, a drying agent could be attached to the fibers of a web like the liner or to a superabsorbent/pulp layer through the use of an adhesive or binder.

It is thus explained that placing a drying agent in a personal care product can reduce or maintain air relative humidity within the product and so reduce skin hydration. This reduced skin hydration is believed to result in reduced skin redness and irritation.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means plus function claims are intended to cover the structures described herein as performing the recited function and not only structural equivalents but also equivalent structures. Thus although a nail and a screw may not be structural equivalents in that a nail employs a cylindrical surface to secure wooden parts together, whereas a screw employs a helical surface, in the environment of fastening wooden parts, a nail and a screw may be equivalent structures.

What is claimed is:

1. A personal care product selected from the group consisting of diapers, training pants, absorbent underpants and adult incontinence products comprising a drying agent selected from the group consisting of $P_2O_5$, $Mg(ClO_4)_2$, $BaO$, $KOH$, $CaO$, $Al_2O_3$, $NaOH$, $CaBr_2$, $CaCl_2$, $Ba(ClO_4)_2$, $ZnCl_2$, $ZnBr_2$, glycerin, sorbitol, glycols, fructose, glucose, maltose, corn syrup, and urea, wherein said drying agent is contained in a liquid impermeable, vapor permeable bag.

2. The personal care product of claim 1 wherein said drying agent is a combination of a desiccant and a humectant.

3. The product of claim 1 wherein said personal care product is an adult incontinence product.

4. The product of claim 1 wherein said personal care product is a diaper.

5. The product of claim 1 wherein said personal care product is a training pant.

6. The personal care product of claim 1 wherein said drying agent will reduce the relative humidity in the air in said product to less than 85 percent.

7. The personal care product of claim 1 wherein said drying agent will maintain relative humidity within said product at a level of less than about 85 percent.

* * * * *

UNITED STATES PATENT AND TRADEMARK OFFICE
CERTIFICATE OF CORRECTION

PATENT NO.   : 6,281,407 B1
DATED        : August 28, 2001
INVENTOR(S)  : Steven B. Warner et al.

It is certified that error appears in the above-identified patent and that said Letters Patent is hereby corrected as shown below:

<u>Title page, Item [54] and Column 1, line 1,</u>
Title, "PERSONAL CARE PRODUCT CONTAINING A PRODUCT AGENT" should read -- PERSONAL CARE PRODUCT CONTAINING A DRYING AGENT --

<u>Column 1,</u>
Line 44, "wearer' " should read -- wearer's --

<u>Column 5,</u>
Line 29, "an is" should read -- an --

<u>Column 6,</u>
Line 53, "modem" should read -- modern --

Signed and Sealed this

Twenty-fourth Day of September, 2002

Attest:

JAMES E. ROGAN
*Attesting Officer*  *Director of the United States Patent and Trademark Office*